ABSTRACT

United States Patent [19]

Chen et al.

[11] 4,336,052

[45] Jun. 22, 1982

[54] METHOD OF USING CORN SYRUP FOR REDUCING PHYTOTOXICITY OF UREA APPLIED TO PLANTS FOR FOLIAR FERTILIZATION

[75] Inventors: Tsong M. Chen, Piscataway; El-Ahmadi I. Heiba, Princeton, both of N.J.; William W. John, Modesto, Calif.

[73] Assignee: Mobil Oil Corporation, New York, N.Y.

[21] Appl. No.: 221,644

[22] Filed: Dec. 31, 1980

[51] Int. Cl.³ ............................................... C05C 9/00
[52] U.S. Cl. ......................................... 71/28; 71/64.8; 71/DIG. 1
[58] Field of Search ..................... 71/1, 11, 25, 28–30, 71/64.8, 64.1, DIG. 1

[56] References Cited

U.S. PATENT DOCUMENTS 4,033,745  7/1977  Moore ............................. 71/64.8 X Primary Examiner—S. Leon Bashore, Jr.
Assistant Examiner—Ferris H. Lander
Attorney, Agent, or Firm—Charles A. Huggett; Michael G. Gilman; Edward J. Trojnar

[57] ABSTRACT

Urea damage to the foliage of plants, particularly legumes such as soybeans, is reduced by application of corn syrup together with urea to the plant leaves.

9 Claims, No Drawings

METHOD OF USING CORN SYRUP FOR REDUCING PHYTOTOXICITY OF UREA APPLIED TO PLANTS FOR FOLIAR FERTILIZATION

SUMMARY OF THE INVENTION

This invention relates to a method for reducing phytotoxicity of urea applied to the leaves of plants. Urea is a known foliar fertilizer for plants such as soybeans but is phytotoxic causing leaf damage, the ultimate effect of which can be yield reduction. In accordance with this invention urea is applied to plants along with corn syrup, to reduce phytotoxicity.

DETAILED DESCRIPTION OF THE INVENTION

The experimental use of urea as a foliar fertilizer for increasing the yield of soybeans has been reported. Although yield increases have been achieved, this practice has not generally been accepted due to a high degree of phytotoxicity and resultant yield loss which often accompanies foliar application of urea. Agronomy Journal 68,653 (1976), Farm Chemicals 140 (3), 32 (1977). Patents have also disclosed the use of urea as a foliar fertilizer. For example, U.S. Pat. Nos. 3,087,806, 4,038,064 and 4,146,383 disclose various foliar fertilizer compositions containing urea. The foregoing patents and articles are not concerned with reduction of phytotoxicity or means to improve the safety of foliar application of urea by the use of additives. The use of sucrose with urea in the foliar fertilization of tomato plants is disclosed in Plant Physiology, 28; 70–76 (1953).

When urea is sprayed on the foliage of plants, such as soybeans, the urea is rapidly taken up into the leaf tissue. This rapid uptake typically results in severe osmotic desiccatation and death of the tissue. The prior practice for reducing phytotoxicity generally consisted of reducing the dose rate to avoid leaf damage.

In accordance with this invention, the rate of urea uptake is reduced by incorporating corn syrup in the urea containing composition. The addition of a corn syrup to the foliar fertilizer composition is believed to result in a more favorable osmotic balance in the tissue and results in reduced leaf damage compared to that observed with the same compositions absent the corn syrup. The inclusion of corn syrup also permits the application of higher doses of urea before toxic symptoms develop.

The amount of urea in the composition applied varies somewhat depending on a number of factors including the crop to be treated, the growth stage at which foliar fertilization is conducted and number of applications which are to be used. The effective amount of urea used, however, generally is in the range of 20 to 60 kg/hectare.

Similarly, the content of the corn syrup can vary widely. Effective amounts of the corn syrup are generally selected so that the minimum amount of corn syrup providing the desired degree of foliar protection against urea damage is present in the treating composition. Typically, the weight ratio of urea to corn syrup effective to achieve the objects of this invention is in the range of 20:1 to 2:1; more commonly in the range of 15:1 to 4:1.

The urea composition containing corn syrup can be applied from $R_2$ to $R_7$ stages of growth. Multiple applications appear to give a better yield response than a single application.

Ingredients other than urea and corn syrup are not required but can be added. For example, other essential nutrients and ingredients such as urease inhibitors can be present with beneficial results. Ingredients which are phytotoxic in themselves should be excluded. It has been found, for example, that many surfactants shown adverse phytotoxic effects and such surfactants should be excluded.

For soybeans the reproductive stages $R_2$ to $R_7$, referred to above, are defined by Fehr et al.; *Crop Science*, 11, 929–931 (November-December 1971) as follows:

| REPRODUCTIVE STAGES | |
|---|---|
| Stage No. | Description |
| $R_1$ | One flower at any node. |
| $R_2$ | Flower at node immediately below the uppermost node with a completely unrolled leaf. |
| $R_3$ | Pod 0.5 cm (¼ inch) long at one of the four uppermost nodes with a completely unrolled leaf. |
| $R_4$ | Pod 2 cm (¾ inch) long at one of the four uppermost nodes with a completely unrolled leaf. |
| $R_5$ | Beans beginning to develop (can be felt when the pod is squeezed) at one of the four uppermost nodes with a completely unrolled leaf. |
| $R_6$ | Pod containing full size green beans at one of the four uppermost nodes with a completely unrolled leaf. |
| $R_7$ | Pods yellowing; 50% of leaves yellow. Physiological maturity. |
| $R_8$ | 95% of pods brown. Harvest maturity |

The present invention provides a method for reducing phytotoxic leaf damage to plants susceptible to urea foliar fertilization, such as corn and legumes, particularly soybeans.

The following examples illustrate the effects which have been observed with combinations of urea and corn syrup. Unless otherwise specified, amounts are in parts by weight.

EXAMPLE 1

This example illustrates the effect of corn syrup at differing concentrations in inhibiting soybean leaf damage by urea applied to foliage.

To prepare stock solution an adequate amount of the test compound was dissolved in water (heat was applied to effect solubilization where necessary). The stock solution was then diluted to the desired concentration in 1 ml of 0.1% Tween-20 in $H_2O$. This test solution was then spiked with 10 µl of 100 mM $^{14}C$-urea (sp. act. 0.51 Ci/mole) to give a 1 mM $^{14}C$-urea test solution. The water used was deionized water prepared with a Barnstead Nanopure Deionizer. Tween-20 is polyoxyethylene (20) sorbitan monolamate.

To assay the effect of the test compound on urea uptake, a fully expanded leaf near the top (4 or 5 nodes from the stem apex) was selected and marked for the test. A 10 µl droplet of the test solution was then placed on the leaf surface at the indicated spot. After a 3-hour uptake period the residual material remaining on the leaf surface was removed with three 25 µl $H_2O$ washes and placed in a scintillation counting vial which contained 1 ml of $H_2O$. To this solution was added 10 ml of Aquasol-2 counting cocktail (NEN) and after thorough mixing the $^{14}C$ in the solution counted with a liquid scintillation counter (Packard Tricarb Liquid Scintillation Spectrometer model 3255). The counting efficiency for the sample was determined by the channels ratio method and cpm were converted to dpm for each sample.

Results are summarized in Table 1.

TABLE 1

| Treatment | | % Uptake | % remaining on surface | % Inhibition |
|---|---|---|---|---|
| Urea + (control) | | 84 | 16 | 0 |
| Urea + corn syrup | (1%) | 40 | 60 | 44 |
| | (8%) | 29 | 71 | 55 |

EXAMPLE 2

This example illustrates the prevention of urea induced phytotoxicity on soybean leaves of growth chamber plants.

The water was deionized water as used in Example 1. No surfactant was present.

A stock solution of urea was prepared. This was then diluted to 3, 6 and 9% urea±2% corn syrup and sprayed on the test plants with a glass atomizer.

Soybean plants were grown in a controlled environment chamber (14-hour photo-period, 27 degrees C. day, 22 degrees night, 620 Ei.M$^{-2}$. sec$^{-1}$) with a step gradient program to simulate daily temperature changes. When the plants were 30 days old they were sprayed with 2 ml of test solution. After an additional 9 days in the growth chamber they were rated for phytotoxicity.

TABLE 2

| Test Solution | Phytotoxicity Rating* | | |
|---|---|---|---|
| | 3% urea | 6% urea | 9% urea |
| Urea (control) | 1.6 | .8 | 4.1 |
| Urea + 2% corn syrup | 0 | .8 | .9 |

*The rating scale was from 0 (no phytotoxicity) to 5 (severe phytotoxicity).

EXAMPLE 3

This example illustrates the prevention of urea induced phytotoxic damage to soybean leaves of field plants.

Water was tap water. No surfactant was present.

A stock solution of urea was prepared. This was then diluted to give 6%, 12% or 18% urea solutions which contained various concentrations of corn syrup protectants (% is weight/volume).

Soybean plants were grown on a farm near Pennington, New Jersey during the 1979 growing season. The plants were sprayed twice (36 gal/A each application) when the plants were at the $R_2$ and $R_4$ stages of reproductive growth. This coincides with the pod set and early seed filling period to provide additional nitrogen to the plant during the main part of the seed filling stage, $R_5$. Phytotoxicity ratings were made 4-6 days after treatment. The treatments were replicated 4 times in a randomized complete block field design. The data was analyzed by analysis of variance using Duncan's Multiple Range Test for significant difference among treatments. Results are summarized in Table 3.

TABLE 3

| | Urea Formulation | Phytotoxicity Rating* |
|---|---|---|
| Experiment 1 | Urea 12% | 17.3 |
| | Urea 12% + corn syrup 2.4% | 12.0 |
| Experiment 2 | Urea 12% | 17.8 |
| | Urea 12% + corn syrup 2.4% | 5.5** |
| Experiment 3 | Urea 12% | 7.3 |
| | Urea 12% + corn syrup 1.2% | 3.3** |

TABLE 3-continued

| | Urea Formulation | Phytotoxicity Rating* |
|---|---|---|
| | Urea 12% + corn syrup 2.4% | 3.0** |
| Experiment 4 | Urea 6% | 10.2 |
| | Urea 6% + corn syrup 2.4% | 4.5 |
| | Urea 12% | 22.2 |
| | Urea 12% + corn syrup 2.4% | 21.8 |
| | urea 18% | 32.5 |
| | Urea 18% + corn syrup 2.4% | 28.0 |

*Phytotoxicity ratings are 0 (no damage) to 100 (100% leaf area damage).
*Treatment significantly different from control at the 95% confidence level.

EXAMPLE 4

This example illustrates the effect of urea compositions with and without added corn syrup on yield in field grown soybeans.

Solution preparation and treatment of plants was as in Example 3. When the treated plants were mature the plots were harvested. The seed was weighed and a moisture determination made. After adjusting the seed weight to 13% moisture content the yield in bushel per acre was calculated. Results are tabulated in Table 4.

TABLE 4

| Experiment | Urea Formulation | Yield | | Percent of Control |
|---|---|---|---|---|
| | | bu/A | l/hectare | |
| 1 | Control | 32.2 | 2803 | 100 |
| | Urea 12% | 34.6 | 3012 | 107 |
| | Urea 12% + corn syrup 2.4% | 33.0 | 2872 | 102 |
| 2 | Control | 35.4 | 3081 | 100 |
| | Urea 12% | 32.0 | 2785 | 90 |
| | Urea 12% + corn syrup 2.4% | 36.0 | 3134 | 102 |
| 3 | Control | 27.1 | 2359 | 100 |
| | Urea 12% | 26.7 | 2324 | 98 |
| | Urea 12% + corn syrup 1.2% | 24.8 | 2159 | 92 |
| | Urea 12% + corn syrup 2.4% | 26.4 | 2298 | 97 |
| 4 | Control | 32.4 | 2820 | 100 |
| | Urea 6% | 34.7 | 3020 | 107 |
| | Urea 6% + corn syrup 2.4% | 36.8 | 3203 | 114 |
| | Urea 12% | 28.4 | 2472 | 88 |
| | Urea 12% + corn syrup 2.4% | 32.6 | 2838 | 101 |
| | Urea 18% | 29.0 | 2524 | 90 |
| | Urea 18% + corn syrup 2.4% | 32.2 | 2803 | 99 |

We claim:

1. A method for reducing phytotoxicity of urea applied as a foliar fertilizer to soybean plants comprising applying to the leaves of said plants an aqueous composition comprising an amount of urea effective as a foliar fertilizer and corn syrup in an amount effective to reduce the leaf damage observed with foliar application of urea in the absence of the corn syrup.

2. The method of claim 1 in which the weight ratio of urea to corn syrup is from 20:1 to 2:1.

3. The method of claim 1 in which said aqueous composition is applied several times during the growing season.

4. The method of claim 1 in which the amount of urea applied is from about 10 to 100 kg/hectare.

5. The method of claim 1 in which the amount of urea applied is 20 to 60 kg/hectare and the weight ratio of urea to corn syrup is from 15:1 to 4:1.

6. The method of claim 1 in which said aqueous composition is surfactant free.

7. The method of claim 1 in which said plants are soybeans, the amount of urea applied is from 10 to 100 kg/hectare, and the weight ratio of urea to corn syrup is from 15:1 to 4:1.

8. The method of claim 1 in which said aqueous composition contains, in addition, urease inhibitor.

9. The method of claim 1 in which said aqueous composition contains, in addition, one or more nutrients selected from the group consisting of potassium polyphosphate, ammonium phosphoroamidate and potassium sulfate.

* * * * *